(12) United States Patent
Ariza

(10) Patent No.: US 9,907,627 B2
(45) Date of Patent: Mar. 6, 2018

(54) ORTHODONTICS SYSTEM AND METHOD OF USE

(71) Applicant: Joaquin T. Ariza, Bogota (CO)

(72) Inventor: Joaquin T. Ariza, Bogota (CO)

( * ) Notice: Subject to any disclaimer, the term of this patent is extended or adjusted under 35 U.S.C. 154(b) by 381 days.

(21) Appl. No.: 14/581,021

(22) Filed: Dec. 23, 2014

(65) Prior Publication Data

US 2015/0111166 A1   Apr. 23, 2015

Related U.S. Application Data

(60) Continuation-in-part of application No. 14/300,975, filed on Jun. 10, 2014, which is a division of application No. 12/548,407, filed on Aug. 26, 2009, now abandoned.

(51) Int. Cl.
*A61C 3/00* (2006.01)
*A61C 7/28* (2006.01)

(52) U.S. Cl.
CPC ......... *A61C 7/282* (2013.01); *Y10T 29/49568* (2015.01)

(58) Field of Classification Search
CPC .............................................. A61C 7/12–7/34
USPC ...................................................... 433/8–24
See application file for complete search history.

(56) References Cited

U.S. PATENT DOCUMENTS

| 4,936,774 | A | * | 6/1990 | Stoller | A61C 7/12 |
| | | | | | 433/110 |
| 5,350,203 | A | * | 9/1994 | McNaughton | F16L 33/2075 |
| | | | | | 285/305 |
| 6,575,747 | B1 | * | 6/2003 | Riitano | A61C 5/44 |
| | | | | | 433/102 |
| 6,779,937 | B1 | * | 8/2004 | Lombardi | A45D 40/205 |
| | | | | | 401/6 |
| 2002/0187453 | A1 | * | 12/2002 | Clark | A61C 7/00 |
| | | | | | 433/18 |
| 2004/0029067 | A1 | * | 2/2004 | Wool | A61C 7/20 |
| | | | | | 433/20 |
| 2004/0154133 | A1 | * | 8/2004 | Polzin | B25F 5/006 |
| | | | | | 16/430 |
| 2004/0157184 | A1 | * | 8/2004 | Reising | A61C 7/146 |
| | | | | | 433/8 |
| 2004/0259054 | A1 | * | 12/2004 | Mayer | A61C 17/20 |
| | | | | | 433/119 |
| 2005/0003324 | A1 | * | 1/2005 | Reising | A61C 7/146 |
| | | | | | 433/50 |
| 2005/0244777 | A1 | * | 11/2005 | Schultz | A61C 7/282 |
| | | | | | 433/17 |

(Continued)

OTHER PUBLICATIONS

Office Action dated Feb. 19, 2016 in U.S. Appl. No. 14/300,975.

*Primary Examiner* — Matthew Nelson
(74) *Attorney, Agent, or Firm* — Jafari Law Group, Inc.

(57) ABSTRACT

The present disclosure relates to an orthodontic system and a method of using the same to perform orthodontics. In one example, an orthodontic system is presented. The orthodontic system includes a tube having at least one sidewall and two opening ends, and a luting agent. The luting agent is disposed on at least a portion of one or more of the at least one sidewall of the tube and a portion of a surface of a tooth onto which the tube is directly attached or adhered. The two opening ends of the tube remain substantially open so that a wire can move along the tube.

23 Claims, 10 Drawing Sheets

(56) References Cited

U.S. PATENT DOCUMENTS

| | | | |
|---|---|---|---|
| 2006/0084032 A1* | 4/2006 | Tipton | A61C 3/00 433/141 |
| 2006/0110703 A1* | 5/2006 | Bills | A61C 5/42 433/102 |
| 2007/0087302 A1* | 4/2007 | Reising | A61C 7/146 433/24 |
| 2011/0039225 A1* | 2/2011 | Hagelganz | A61C 7/14 433/17 |

* cited by examiner

FIG. 1A
FIG. 1B
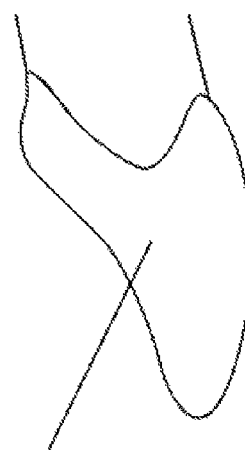
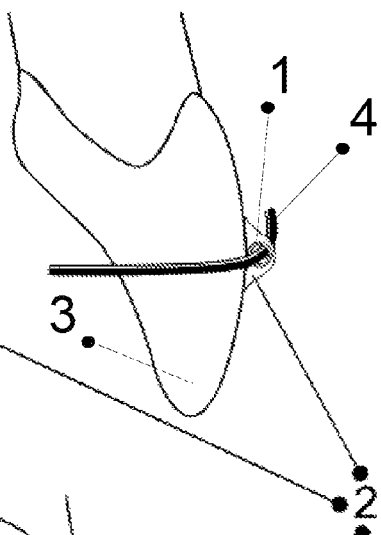
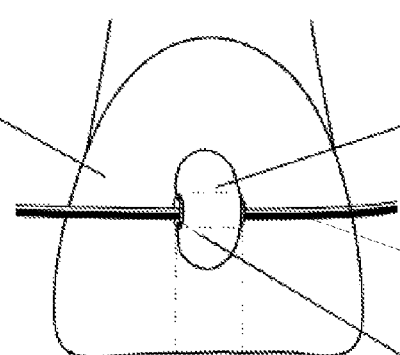
FIG. 1C
FIG. 1D

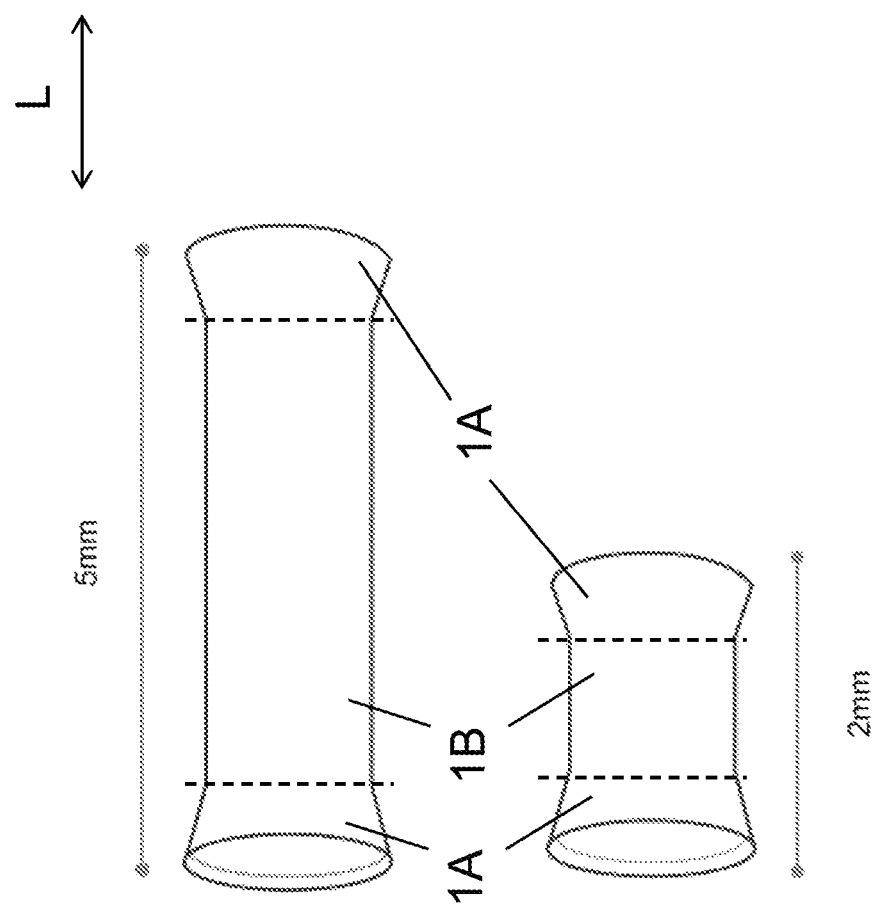

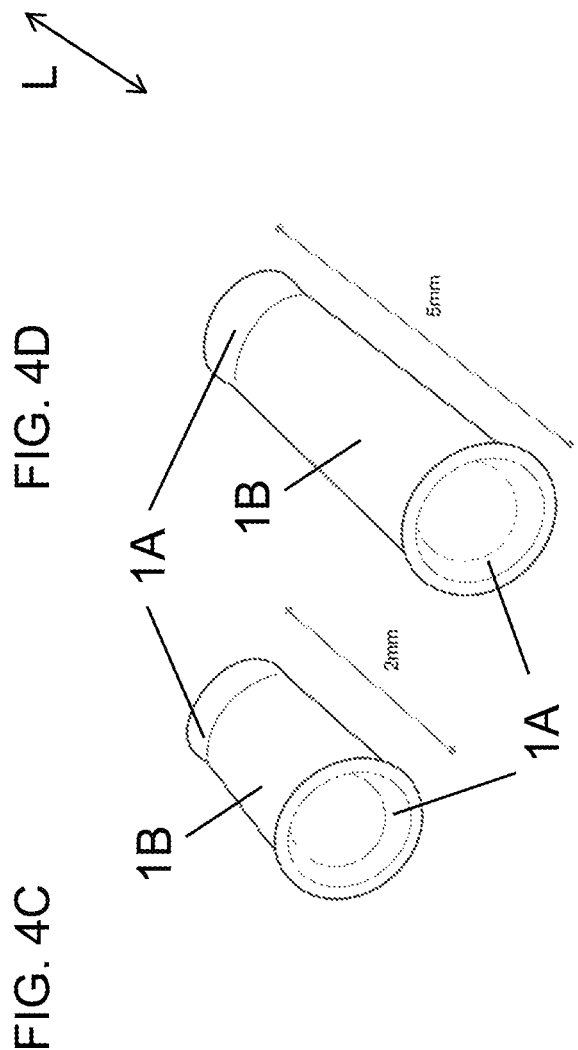

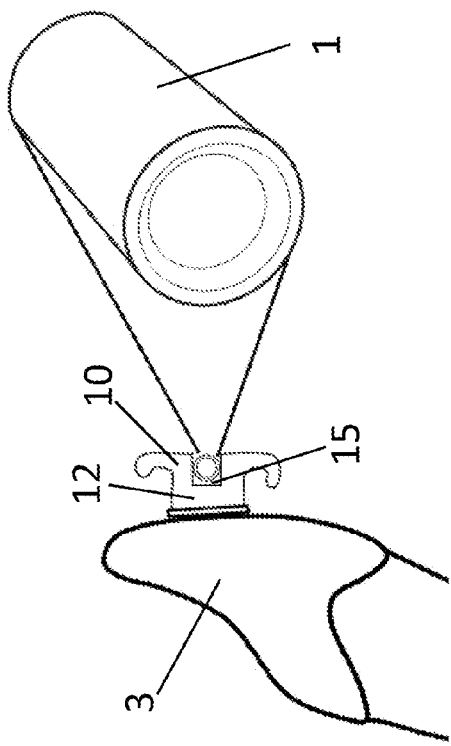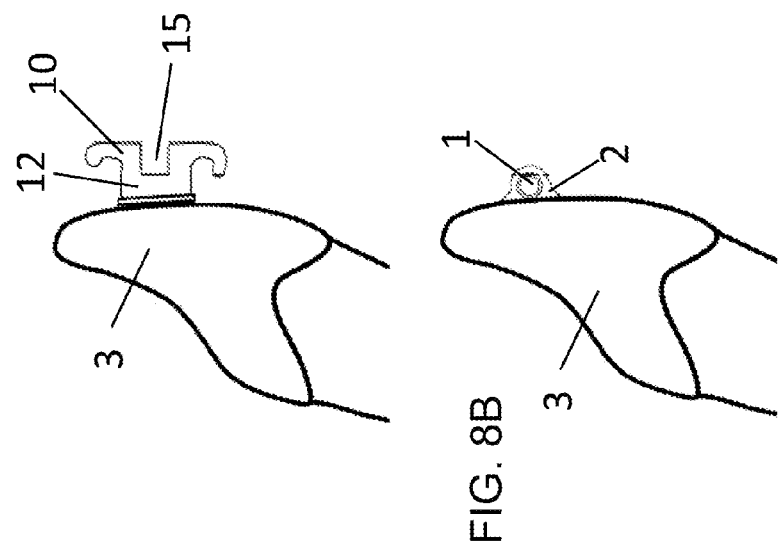

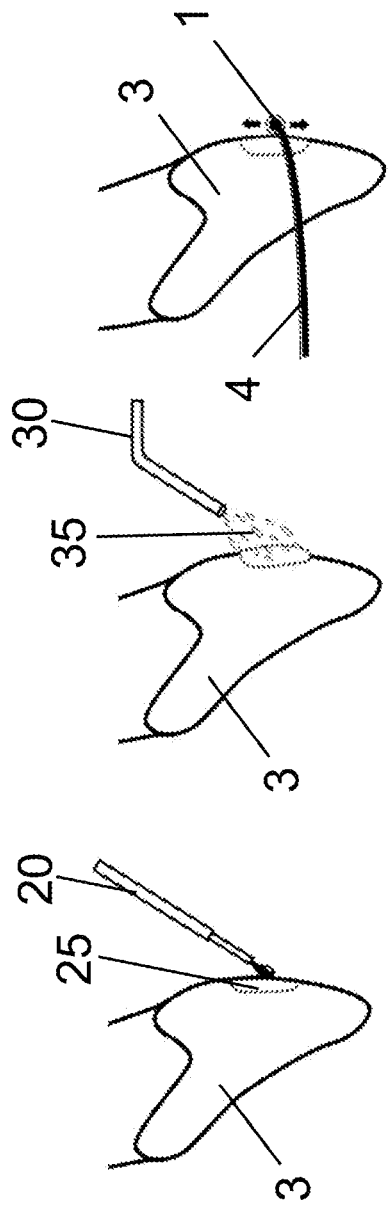
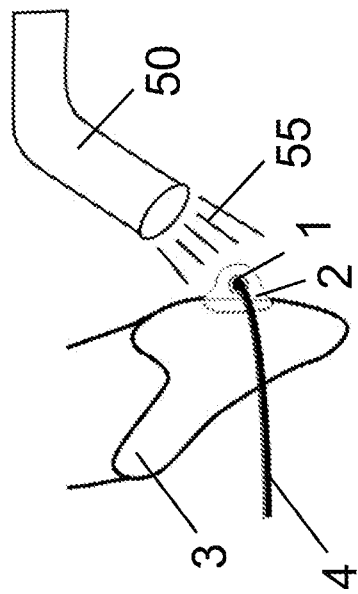
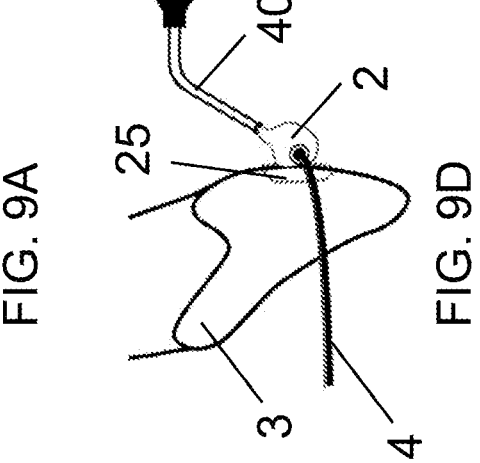

ORTHODONTICS SYSTEM AND METHOD OF USE

CROSS-REFERENCE TO RELATED APPLICATIONS

The present application is a continuation-in-part claiming the benefit of priority to U.S. patent application Ser. No. 14/300,975, filed Jun. 10, 2014, which in turn is a divisional application claiming the benefit of priority to U.S. patent application Ser. No. 12/548,407, filed Aug. 26, 2009, now abandoned, each of which is hereby incorporated by reference.

BACKGROUND

1. Technical Field

The present disclosure relates to dentistry. Specifically, the present disclosure relates to an orthodontic system and a method of using the same to perform orthodontics.

2. Discussion of Technical Background

Orthodontics, a branch of dentistry, deals with misalignment of teeth and their correction. Misalignment of teeth may be at least partially corrected by imparting forces to the teeth over a period of time to bring about movements of the teeth toward desired positions. An orthodontic system may be used in such a procedure. An orthodontic system may include, e.g., a wire configured to exert forces, and structural components configured to impart the forces to the teeth involved in the procedure.

Historically, the process of orthodontics to place brackets involves a number of steps and procedures that not only increase the time to attend a patient in a clinical appointment and the likelihood of errors in each step performed by the orthodontist but also may increase the discomfort of the patient. This is at least partially due to the complex shape and the big size of the conventional appliances (brackets), which makes difficult to try to simplify the processes involved.

Additionally, the processes of placing and bonding these big conventional appliances (brackets) need high adhesive forces to sustain not only its own weight and volume but the anchorage of the wires and the auxiliary elements of the orthodontics (elastics, hooks complementary support and devices, among others) moreover the system has to be maintained in place during the chewing forces while the patient eats.

Therefore, there is a need to develop an improved orthodontic system and method to solve the above-mentioned problems.

SUMMARY

The teachings disclosed herein relate to an orthodontic system and a method of using the same to perform orthodontics, including a method of placing and bonding the orthodontic system to the teeth of a patient.

In one example, an orthodontic system is presented. The orthodontic system includes a tube having at least one sidewall and two opening ends, and a luting agent. The luting agent is disposed on at least a portion of one or more of the at least one sidewall of the tube and a portion of a surface of a tooth onto which the tube is directly attached or adhered. The two opening ends of the tube remain substantially open so that a wire can move along the tube.

In another example, an orthodontic system is presented. The orthodontic system includes a tube having at least one sidewall and two opening ends. One or more of the at least one sidewall having a pre-applied luting agent. One of the one or more sidewalls can be pressed against a surface of a tooth so that the pre-applied luting agent attaches the tube directly onto the surface of the tooth. The two opening ends of the tube remain substantially open so that a wire can move along the tube.

In a different example, a method for performing orthodontics is presented. The method includes providing a plurality of tubes each of which has at least one sidewall and two opening ends; and for each of the plurality of tubes, depositing a luting agent on at least a portion of one or more of the at least one sidewall of the tube and a portion of a surface of a tooth onto which the tube is directly attached or adhere, and curing the luting agent. The two opening ends of each tube remain substantially open so that a wire can move along the tube.

In a further example, a method for performing orthodontics is presented. The method includes providing a plurality of tubes each of which has at least one sidewall and two opening ends, one or more of the at least one sidewall having a pre-applied luting agent; and for each of the plurality of tubes, pressing one of the one or more of the at least one sidewall against a surface of a tooth so that the pre-applied luting agent attaches the tube directly onto the surface, and curing the pre-applied luting agent. The two opening ends of each tube remain substantially open so that a wire can move along the tube.

In still a further example, a method for providing a tube is presented. The method includes receiving information related to an orthodontic treatment on one or more teeth of a patient; and providing, based on the information, the tube to be used in the orthodontic treatment, the tube having at least one sidewall and two opening ends. The tube is configured to be directly attached to a surface of a tooth of the patient using a luting agent, and the two opening ends of the tube remain substantially open so that a wire can move along the tube.

BRIEF DESCRIPTION OF THE DRAWINGS

The orthodontic system and the method of putting and using the same to perform orthodontics as disclosed herein are further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 1A illustrates a lateral view of a tooth that is treated with an orthodontic system according to some embodiments of the present disclosure;

FIG. 1B illustrates a lateral view of a tooth that is treated with an orthodontic system according to some embodiments of the present disclosure, in which a wire is shown;

FIG. 1C illustrates a frontal view of a tooth that is treated with an orthodontic system according to some embodiments of the present disclosure, in which a wire is shown;

FIG. 1D illustrates a tube included in an orthodontic system according to some embodiments of the present disclosure;

FIGS. 2A-4D illustrate various embodiments of a tube disclosed herein;

FIG. 8A illustrates a lateral view of a tooth that is treated with a conventional orthodontic system including a bracket;

FIG. 8B illustrates a lateral view of a tooth that is treated with an orthodontic system according to some embodiments of the present disclosure;

FIG. 8C illustrates a lateral view of a tooth that is treated with a conventional orthodontic system including a bracket, in which the size of the slot of the bracket is comparable to the size of a tube according to some embodiments of the present disclosure; and FIGS. 9A-9E illustrate a method of putting and using the orthodontic system according to some embodiments of the present disclosure.

DETAILED DESCRIPTION

Figure 2A:
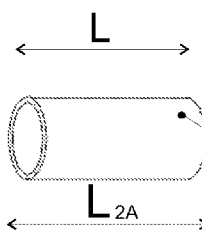
Figure 2B:
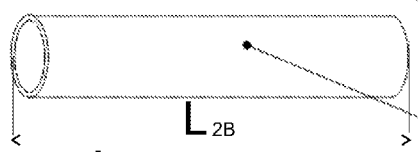

In the following detailed description, numerous specific details are set forth by way of examples in order to provide a thorough understanding of the relevant teachings. However, it should be apparent to those skilled in the art that the present teachings may be practiced without such details. In other instances, well known structures, components and/or functional or structural relationship thereof, etc., have been described at a relatively high-level, without detail, in order to avoid unnecessarily obscuring aspects of the present teachings.

Throughout the specification and claims, terms may have nuanced meanings suggested or implied in context beyond an explicitly stated meaning Likewise, the phrase "in one embodiment/example" as used herein does not necessarily refer to the same embodiment and the phrase "in another embodiment/example" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The present disclosure relates to, among other things, an orthodontic system and a method of using the same to perform orthodontics, including a method of placing and bonding the orthodontic system to the teeth of a patient. Exemplary embodiments of the present disclosure are described with reference to the drawings for illustration purposes, and are not intended to limit the scope of the present disclosure.

FIGS. 1A-1D illustrate lateral and frontal views of a tooth that is treated with an orthodontic system according to some embodiments of the present disclosure. Specifically, FIG. 1A illustrates a lateral view of a tooth that is treated with an orthodontic system according to some embodiments of the present disclosure; FIG. 1B illustrates a lateral view of a tooth that is treated with an orthodontic system according to some embodiments of the present disclosure, in which a wire is shown; FIG. 1C illustrates a frontal view of a tooth that is treated with an orthodontic system according to some embodiments of the present disclosure, in which a wire is shown; and FIG. 1D illustrates a tube included in an orthodontic system according to some embodiments of the present disclosure. The exemplary orthodontic system may include a tube 1 and a luting agent 2 (also referred to as the luting surround agent). The tube 1 may be directly attached to a surface of the tooth 3 by the luting agent 2, indicating that one or more sidewalls of the tube 1 either directly contact the surface of the tooth 3, or are separated from the surface of the tooth 3 by the luting agent 2, and there are no other structural components like, e.g., a base, located between or otherwise involved in the attachment of the one or more sidewalls of the tube and the surface of the tooth. The tube 1 may have at least one sidewall and two opening ends. The tube 1 may be substantially surrounded by or embedded or supported in the luting agent 2 disposed on at least a portion of the at least one sidewall of the tube 1. The two opening ends of the tube 1 may remain substantially open so that a wire 4 may go through and/or move along the tube 1.

In some embodiments, a tube may have at least one sidewall and two opening ends. A sidewall of a tube may have an inner wall and an outer wall. The inner wall(s) of the at least one sidewall may define and face the tubular passage of the tube. The tubular passage of the tube may allow a wire to go through the tube and/or move along it, as discussed elsewhere in the application. The outer wall(s) of the at least one sidewall may face the ambient surrounding the tube. As used herein, an outer cross-section of a tube refers to the surface and/or shape defined by the outer wall(s) of the at least one sidewall. A cross-section of a tube may have an annular shape defined by the inner wall(s) and the outer wall(s) of the at least one sidewall of the tube. That is, a cross-section of a tube may be defined by the cross-section of the tubular passage and the outer cross-section. The shape of the tubular passage may be, e.g., a circle, a polygon (e.g., a triangle, a rectangle, a square, a pentagon, a hexagon), an oval, or the like. The polygon may have one or more rounded corners. The shape of the tubular passage may be chosen based on considerations including, e.g., the shape of the wire to be inserted into the tube, friction between the tubular passage and the wire, ease of manufacture, or the like, or a combination thereof. The shape defined by the outer wall(s) (the outer cross-section) of the at least one sidewall of the tube may be, e.g., a circle, a polygon (e.g., a triangle, a rectangle, a square, a pentagon, a hexagon), an oval, or the like. The polygon may have one or more rounded corners. The shape defined by the outer wall(s) (the outer cross-section) of the at least one sidewall of the tube may be chosen based on considerations including, e.g., attachment of the tube to a surface of a tooth, comfort of a patient whose teeth are treated using the orthodontic system including the tubes disclosed herein, visibility of the orthodontic system including the tubes disclosed herein, ease of manufacture, or the like, or a combination thereof. The cross-section of the tubular passage and the outer cross-section may be concentric. The cross-section of the tubular passage and the outer cross-section may be symmetric about a same axis. As used herein, an inner dimension of a cross-section of a tube may refer to the largest dimension of the tubular passage at a cross-section of the tube; and an outer dimension of a cross-section of a tube may refer to the largest dimension of the outer cross-section of the tube.

FIGS. 2A-4D illustrate various embodiments of a tube disclosed herein. The double arrow L indicates the length direction of the tubes shown in these figures. FIG. 2A shows a cylindrical tube 1 with a sidewall and two opening ends. The sidewall may have an outer wall and an inner wall. The inner wall may define the tubular passage. A cross-section of the outer wall may form a first circle (outer cross-section), and a cross-section of the inner wall may form a second circle. At a cross-section of the tube 1, the first circle and the second circle may be concentric. A cross-section of the cylindrical tube 1, defined by the sidewall, may be a ring. At a cross-section of the tube 1, the outer dimension may be the largest dimension of the first circle (outer cross-section), i.e. the diameter of the first circle. The outer dimensions (or perimeters) of outer cross-sections along the length $L_{2A}$ of the tube 1, including the two opening ends, may be constant or substantially constant. As used herein, "substantially constant" indicates that the variation is less than 30%, or less than 25%, or less than 20%, or less than 15%, or less than 10%, or less than 5%. At a cross-section of the tube, the inner dimension may be the largest dimension of the circular tubular passage of the tube, i.e. the diameter of the second circle. The inner dimensions (or perimeters) of cross-sections of the tubular passage along the length $L_{2A}$ of the tube 1, including the two opening ends, may be constant or substantially constant. Except for the sidewall forming the tubular passage, the tube 1 does not have other structural components like, e.g., a base, a notch, a wing, or the like, or a combination thereof. FIG. 2B shows a cylindrical tube 1 with a sidewall and two opening ends. The cylindrical tube 1 shown in FIG. 2B may be the same as that shown in FIG. 2A, except that its length $L_{2B}$ is longer than the length, $L_{2A}$, of the cylindrical tube 1 shown in FIG. 2A.

Figure 2C:
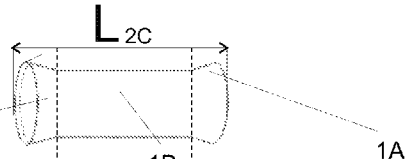

FIG. 2C shows a tube 1 with a sidewall and two opening ends. The sidewall may have an outer wall and an inner wall. The inner wall may define the tubular passage. A cross-section of the outer wall may form a first circle (outer cross-section), and a cross-section of the inner wall may form a second circle. A cross-section of the tube 1, defined by the sidewall, may be a ring. At a cross-section of the tube 1, the first circle and the second circle may be concentric. The tube 1 may have a trumpet shape toward an opening end. The tube 1 as illustrated in FIG. 2C may have a middle section 1B (the section between the two dashed lines) located between two flared end sections 1A. The middle section 1B may be similar to the tubes 1 shown in FIGS. 2A and 2B. In the middle section 1B, the outer dimensions (or perimeters) of outer cross-sections along the length $L_{2C}$ of the tube 1 may be constant or substantially constant; and the inner dimensions (or perimeters) of cross-sections of the tubular passage along the length $L_{2C}$ of the tube 1 may be constant or substantially constant. In a flared end section 1A, the outer dimensions (or perimeters) of outer cross-sections may decrease along the length $L_{2C}$ of the tube 1 from the opening end toward the middle section 1B; and the inner dimensions (or perimeters) of cross-sections of the tubular passage may decrease along the length $L_{2C}$ of the tube 1 from the opening end toward the middle section 1B. The inner dimension (or perimeter) of an opening end (the diameter or perimeter of the tubular passage at the opening end) may be larger than the inner dimension (or perimeter) of a cross-section in the rest of the flared end section 1A of the tube 1. The inner dimension (or perimeter) of an opening end (the diameter or perimeter of the tubular passage at the opening end) may be larger than the inner dimension (or perimeter) of a cross-section in the middle section 1B of the tube 1. From an opening end toward the middle section 1B (between the two opening ends) along the length $L_{2C}$ of the tube 1, the outer dimensions (or perimeters) of the outer cross-sections may decrease in the flared end sections 1A and then remain constant or substantially constant in the middle section 1B. From an opening end toward the middle section 1B (between the two opening ends) along the length $L_{2C}$ of the tube 1, the outer dimensions (or perimeters) of the outer cross-sections of the tube may change in the flared end sections 1A and then remain constant or substantially constant in the middle section 1B. The change (e.g., increase, decrease) in the outer dimensions (or perimeters) of the outer cross-sections in a flared end section 1A may be gradual, or not gradual. Merely by way of example, the outer dimensions (or perimeters) of the outer cross-sections in a flared end section 1A may decrease gradually in some part(s) of the flared end section 1A, and may change abruptly in other part(s) of the flared end section 1A. As another example, the outer dimensions (or perimeters) of the outer cross-sections in a flared end section 1A may be constant or substantially constant in some part(s) of the flared end section 1A, and may change gradually or abruptly in other part(s) of the flared end section 1A. From an opening end toward the middle section 1B (between the two opening ends) along the length $L_{2C}$ of the tube 1, the inner dimensions (or perimeters) of the cross-sections of the tubular passage may decrease in the flared end sections 1A and then remain constant or substantially constant in the middle section 1B. The decrease in the inner dimensions (or perimeters) of the cross-sections of the tubular passage in a flared end section 1A may be gradual to avoid a sharp edge in the tubular passage in the flared end section 1A. The transition from the middle section 1B to the flared end section 1A may be smooth to avoid a sharp edge in the tubular passage at the interface of the middle section 1B and the flared end section 1A. A flared end section can improve the system performance when the tube is attached to the tooth surface by a luting agent.

Figure 2D:
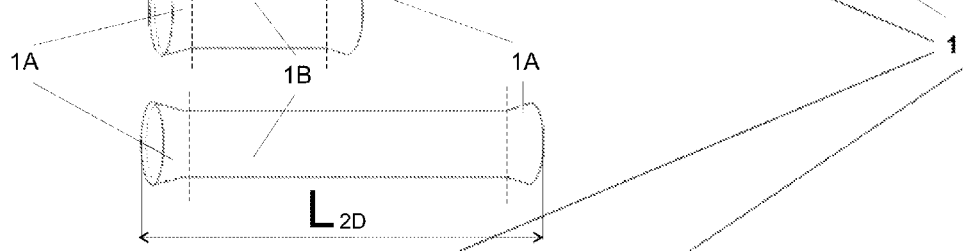

Merely by way of example, a flared end section may help prevent that the tube from slipping laterally into the luting agent when this has already hardened. Additionally, it may prevent the luting agent in the flowable state, from leaking to any of the two ends of the tube, blocking the insertion and the free sliding of the wire through the tube. A flared end section may facilitate the insertion of a wire into the tube. A flared end section may reduce the friction between the wire and the edge of the opening end, thereby allowing, e.g., a smooth sliding of the wire within the tube, when for example the orientation of two tubes are different due to misalignment of the teeth to which the tubes are fixed. Except for the sidewall forming the tubular passage, the tube does not have other structural components like, e.g., a base, a notch, a wing, or the like, or a combination thereof. FIG. 2D shows a tube with a sidewall and two opening ends. The tube shown in FIG. 2D may be the same as that shown in FIG.

2C, except that its length $L_{2D}$ is longer than the length, $L_{2C}$, of the tube shown in FIG. 2C.

Figure 2E:
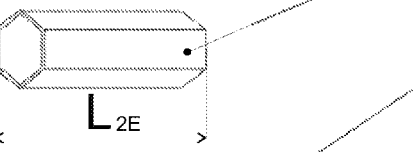
Figure 2F:
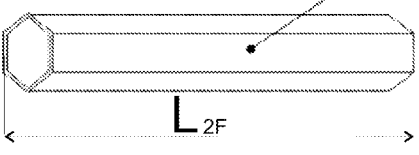

FIG. 2E shows a tube 1 with six sidewalls and two opening ends. A sidewall may have an outer wall and an inner wall. The inner walls of the six sidewalls may define the tubular passage. A cross-section of the outer walls may form a first hexagon (outer cross-section), and a cross-section of the inner walls may form a second hexagon. At a cross-section of the tube 1, the first hexagon and the second hexagon may be symmetric about a same axis. The cross-section of the tube 1 may be an annular hexagon. At a cross-section of the tube 1, the outer dimension may be the largest dimension of the first hexagon defined by the six outer walls of the tube (outer cross-section). The outer dimensions (or perimeters) of outer cross-sections along the length $L_{2E}$ of the tube 1, including the two opening ends, may be constant or substantially constant. At a cross-section of the tube, the inner dimension may be the largest dimension of the hexagonal tubular passage of the tube 1, i.e. the second hexagon. The inner dimensions (or perimeters) of cross-sections of the tubular passage along the length $L_{2E}$ of the tube 1, including the two opening ends, may be constant or substantially constant. Except for the sidewalls forming the tubular passage, the tube does not have other structural components like, e.g., a base, a notch, a wing, or the like, or a combination thereof. FIG. 2F shows a tube 1 with six sidewalls and two opening ends. The tube 1 shown in FIG. 2F may be the same as that shown in FIG. 2E, except that its length $L_{2F}$ is longer than the length, $L_{2E}$, of the tube 1 shown in FIG. 2E. It is understood that the tube 1 as illustrated in FIG. 2E or FIG. 2F may include one or more flared end sections similar to those illustrated in FIGS. 2C and 2D.

As a further example, a tube may have two sidewalls and two opening ends. A sidewall may have an outer wall and an inner wall. The inner walls of the two sidewalls may define the tubular passage. A cross-section of the outer walls may form a first half-oval, and a cross-section of the inner walls may form a second half-oval. A first half-oval may have a first long axis, and a first short axis. A second half-oval may have a second long axis, and a second short axis. At a cross-section of the tube, the first short axis and the second short axis may coincide, and the first half-oval and the second half-oval may be symmetric about the first/second short axis. At a cross-section of a tube, the outer dimension may be the largest dimension of the first half-oval (outer cross-section), i.e. the largest dimension along the first long axis of the first half-oval. At a cross-section of a tube, the inner dimension may be the largest dimension of the tubular passage of the tube, i.e. the largest dimension along the second long axis of the second half-oval. The outer dimensions (or perimeters) of the outer cross-sections along the length of the tube, including the two opening ends, may be constant or substantially constant. The inner dimensions (or perimeters) of cross-sections of the tubular passage along the length of the tube, including the two opening ends, may be constant or substantially constant. The tube may include one or more flared end sections similar to those illustrated in FIGS. 2C and 2D.

At a cross-section of a tube, the cross-section (e.g., shape) of the tubular passage defined by the inner wall(s) may be the same as the cross-section (e.g., shape) defined by the outer wall(s) of the at least one sidewall of a tube (outer cross-section), as illustrated in, e.g., FIGS. 2A-2F. Alternatively, the cross-section (e.g., shape) of the tubular passage defined by the inner wall(s) may be different from the cross-section (e.g., shape) defined by the outer wall(s) of the at least one sidewall of a tube (outer cross-section). E.g., at a cross-section of a tube, the shape of the tubular passage defined by the inner wall(s) may be, e.g., a circle, while the shape defined by the outer wall(s) (outer cross-section) may be, e.g., a polygon (e.g., a triangle, a rectangle, a square, a pentagon, a hexagon), an oval, or the like. The polygon may have one or more rounded corners.

On the other hand, e.g., at a cross-section of a tube, the shape of the tubular passage defined by the outer wall(s) may be, e.g., a circle, while the shape defined by the inner wall(s) (inner cross-section) may be, e.g., a polygon (e.g., a triangle, a rectangle, a square, a pentagon, a hexagon), an oval, or the like. The polygon may have one or more rounded corners.

Figure 3B:
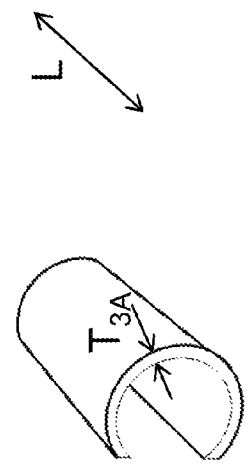
Figure 3A:
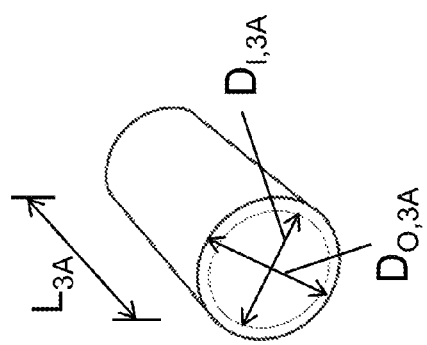

FIG. 3A shows a cylindrical tube with a sidewall and two opening ends. The cylindrical tube shown in FIG. 3A is similar to those shown in FIGS. 2A and 2B. FIG. 3B shows a portion of the sidewall of the cylindrical tube shown in FIG. 3A. The sidewall may have an outer wall and an inner wall. The inner wall may define the tubular passage. A cross-section of the outer wall of the sidewall may form a first circle (outer cross-section), and a cross-section of the inner wall of the sidewall may form a second circle. A cross-section of the cylindrical tube, defined by the sidewall, may be a ring or a partial ring (e.g., a ring without a portion of the sidewall at a cross-section of the tube), the first circle and the second circle may be concentric. At a cross-section of the tube, the outer dimension may be the largest dimension of the first circle (outer cross-section), i.e. the diameter of the first circle $D_{O,3A}$. The outer dimensions (or perimeters) of outer cross-sections along the length $L_{3A}$ of the tube 1, including the two opening ends, may be constant or substantially constant. At a cross-section of the tube, the inner dimension may be the largest dimension of the circular tubular passage of the tube, i.e. the diameter of the second circle $D_{I,3A}$. The inner dimensions (or perimeters) of cross-sections of the tubular passage along the length $L_{3A}$ of the tube, including the two opening ends, may be constant or substantially constant. The thickness of the sidewall $T_{3A}$ of the tube may be half of the difference between $D_{O,3A}$ and $D_{I,3A}$. In some embodiments, the thickness of a sidewall of a tube may be constant or substantially constant along the length of the tube. Except for the sidewall forming the tubular passage, the tube does not have other structural components like, e.g., a base, a notch, a wing, or the like, or a combination thereof.

Figure 3C:
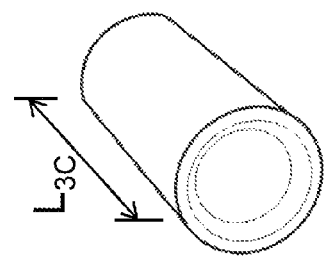

FIG. 3C shows a tube with a sidewall and two opening ends. The tube shown in FIG. 3C is similar to those shown in FIGS. 2C and 2D. The tube may have a middle section between two flared end sections. The middle section of the tube shown in FIG. 3C may be similar to the cylindrical tube shown in FIG. 3A. The transition from the middle section to a flared end section may be smooth such that there is no sharp edge in the tubular passage at the interface between the middle section and the flared end section.

FIGS. 4A-4D show exemplary embodiments of a tube disclosed herein. The tubes shown in FIGS. 4A-4D may be similar to those shown in FIGS. 2C, 2D, and 3C. A tube may have a middle section 1B (the section between the two dashed lines) located between two flared end sections 1A. The tube as illustrated has a length (including the length of the two flared end sections 1A) of 5 millimeters (FIGS. 4A and 4D), or 2 millimeters (FIGS. 4B and 4C). In some embodiments, a tube may have a length shorter than 2 millimeters, e.g., 1.5 millimeters, 1 millimeter, or shorter than 1 millimeter. In some embodiments, a tube may have a length between 2 millimeters and 5 millimeters, e.g., 2.5 millimeters, 3 millimeters, 3.5 millimeters, 4 millimeters, or 4.5 millimeters. In some embodiments, a tube may have a length larger than 5 millimeters, e.g., 5.5 millimeters, 6 millimeters, 6.5 millimeters, or 7 millimeters, or larger than 7 millimeters. A tube may be attached to one or more teeth using a luting agent. The length of a flared end section, if present in a tube, may be, e.g., lower than 5%, 8%, 10%, 15%, 20%, or 30% of the length of a tube. The length of a tube may be chosen based on considerations including, e.g., the size (e.g., the mesiodistal length) of a tooth onto which the tube is attached to, or the like.

In some embodiments, the inner dimension of a tube (or the inner dimension of the middle section of a tube having one or more flared end sections) may be less than 5 millimeters, or less than 4 millimeters, or less than 3 millimeters, or less than 1 millimeter, or less than 0.8 millimeters, or less than 0.6 millimeters, or less than 0.5 millimeters, or less than 0.4 millimeters. In some embodiments, the inner diameter of a tube may be approximately 1 millimeter, or approximately 0.8 millimeters, or approximately 0.6 millimeters, or approximately 0.5 millimeters, or approximately 0.4 millimeters. The inner dimension of the tube may be substantially the same or slightly larger than the dimension of a wire (e.g., the cross-section of the wire) that may go through the tube and may move along the tube, as discussed elsewhere in the application. Merely by way of example, the difference between the inner dimension of the tube and the dimension of the wire may be 0.5%, or 1%, or 2%, or 4%, or 5%, or 6%, or 8%, or 10%, or larger than 10% of the inner dimension of the tube (or the inner dimension of the middle section of a tube having one or more flared end sections). If a tube has one or more flared end sections (see, e.g., FIGS. 2C, 2D, 3C, and 4A-4D), the inner dimension of the middle section may be smaller than the inner dimension of a flared end section thereof. In this situation, the inner dimension of the middle section may provide more constraint on the dimension of a wire than the inner dimension of a flared end section. The difference between the inner dimension of an opening end of a flared end section and the inner dimension of the middle section of the tube may be 0.5%, 1%, 2%, 4%, 5%, 6%, 8%, 10%, 15%, 20%, or larger than 20% of the inner dimension of the middle section of the tube. From an opening end toward the middle section (between the two opening ends) along the length of a tube, the outer dimensions (or perimeters) of outer cross-sections in the flared end section may change. The change (e.g., increase, decrease) in the outer dimensions (or perimeters) of the outer cross-sections in a flared end section may be gradual, or not gradual. Merely by way of example, the outer dimensions (or perimeters) of the outer cross-sections in a flared end section may change gradually in some part(s) of the flared end section, and may change abruptly in other part(s) of the flared end section. As another example, the outer dimensions (or perimeters) of the outer cross-sections in a flared end section may be constant or substantially constant in some part(s) of the flared end section, and may change gradually or abruptly in other part(s) of the flared end section. From an opening end toward the middle section (between the two opening ends) along the length of a tube, the inner dimensions (or perimeters) of the cross-sections of the tubular passage in the flared end section may decrease. The decrease in the inner dimensions (or perimeters) of cross-sections of the tubular passage in a flared end section may be gradual to avoid a sharp edge in the tubular passage in the flared end section. The transition from the middle section to a flared end section may be smooth to avoid a sharp edge in the tubular passage at the interface of the middle section and the flared end section.

In some embodiments, the thickness of the sidewall of a tube may be less than less than 5 millimeters, or less than 4 millimeters, or less than 3 millimeters, or less than 1 millimeter, or less than 0.8 millimeters, or less than 0.6 millimeters, or less than 0.5 millimeters, or less than 0.4 millimeters, or less than 0.3 millimeters, or less than 0.2 millimeters, or less than 0.1 millimeters. In some embodiments, the thickness of a sidewall of a tube may be approximately 1 millimeter, or approximately 0.8 millimeters, or approximately 0.6 millimeters, or approximately 0.5 millimeters, or approximately 0.4 millimeters, or approximately 0.3 millimeters, or approximately 0.2 millimeters, or approximately 0.1 millimeters.

If an orthodontic system to be applied to a patient includes a plurality of tubes, the tubes may have different sizes, e.g., different lengths, inner/outer dimensions, wall thickness, depending on, e.g., the specific sizes of the teeth to which the tubes are to be attached. The tubes may be commercially available, or customarily made for a patient. As used herein, a patient refers to a person to whose teeth an orthodontic system is applied and/or the orthodontics is performed.

In some embodiments, a tube may comprise a metal, e.g., stainless steel, titanium, or the like, or an alloy thereof. Merely by way of example, a tube may comprise a metal with a carbon coating. In some embodiments, a tube may comprise a nonmetallic material, e.g., a ceramic, a polymer, plastics, or the like, or a combination thereof. A ceramic may include, e.g., zirconium dioxide ($ZrO_2$), silicone dioxide, powered quartz, alumina, or the like, or a mixture thereof. Plastics may include, e.g., methyl methacrylate, polycarbonate, polyacrylic, polyethylene, polyester, resin, or the like, or a mixture thereof. A tube may comprise a material that is hard such that the tube may substantially maintain its shape to allow a wire to go through it and/or move along it, as discussed elsewhere in the application.

Also shown in FIGS. 1A-1C is the luting agent 2. The luting agent 2 has a high adhesiveness to the micro-porosities created by the conditioner acid on the tooth surface. The luting agent 2 may attach a tube 1 directly to a surface of the tooth 3. One or more sidewalls of the at least one sidewall of the tube may be attached directly to the surface of the tooth using the luting agent 2, indicating that the one or more sidewalls either directly contact the surface of the tooth 3, or are separated from the surface of the tooth 3 by the luting agent 2, and there are no other structural components like, e.g., a base, located between or otherwise involved in the attachment of the one or more sidewalls of the tube 1 and the surface of the tooth 3. The luting agent 2 may cover at least 30%, 40%, 50%, 60%, 70%, 80%, 90% or more of the surface area (defined by the outer wall(s)) of the at least one sidewall of the tube 1, providing a smooth surface outside of the at least one sidewall of the tube 1. The tube 1 may be substantially surrounded by or embedded in the luting agent 2 while it is attached or adhered directly to a surface of a tooth 3. This attachment may allow a force exerted onto the tube 1 (e.g., by the wire 4, which is discussed elsewhere in the application) to be transmitted to the tooth 3. The force on the tooth 3 may, e.g., at least partially correct misalignment of the tooth 3. The opening ends of the tube 1 may remain substantially open so that the wire 4 may go through and/or move along the tube 1.

The luting agent 2 may include, e.g., flowable resin, or the like. As used herein, resin may include any kind of resin that may be used in dentistry, or a substitute material, e.g., ceramics, ionomer, polymer. The luting agent 2 may have a suitable density as to wet the surface of the tooth, flow smoothly and cover the tube 1 before curing. The luting agent 2 may be light curable, such that it may harden when exposed to light, a process known as light-curing. The luting agent 2 may include a self-cure material, or a dual-cure material. The luting agent 2 may have or be manipulated to have a color that is the same as or similar to the color of the tooth 3.

In some embodiments, a luting agent may be pre-applied to a tube such that the tube may have at least one sidewall and two opening ends, one or more of the at least one sidewall having the pre-applied luting agent. One of the one or more sidewalls may be pressed against a surface of a tooth so that the pre-applied luting agent may attach the tube directly onto the surface of the tooth. The two opening ends may remain substantially open so that a wire may go through and/or move along the tube.

Further shown in FIGS. 1A-1C is the wire 4. The wire 4 may go through and/or move along the tube 1. The wire 4 may distribute or exert forces to a tube directly attached to a surface of a tooth, and the force may be imparted to the tooth. The forces applied to the tooth over a period of time may move the tooth to, e.g., correct its misalignment. The direction of the forces imparted to the tooth 3 may be adjusted by adjusting, e.g., the length of the wire 4, the orientation of the tube 1 directly attached to the surface of the tooth, or the like, or a combination thereof.

The wire 4 may comprise at least one type selected from the group consisting of, e.g. rigid, elastic or super elastic arches. The wire 4 may comprise at least one material selected from the group consisting of, e.g., stainless steel, nickel, titanium, copper, or the like, or an alloy thereof. Merely by way of example, the wire 4 may comprise a nickel-titanium alloy, or an alloy comprising copper, nickel, and titanium. In some embodiments, a wire may comprise a nonmetallic material, e.g., a ceramic, a polymer, plastics, or the like, or a combination thereof. Plastics may include, e.g., methyl methacrylate, polycarbonate, polyacrylic, polyethylene, polyester, resin, or the like, or a mixture thereof. Merely by way of example, a wire may comprise a metal with a carbon coating. The wire 4 may have a cross-section of a circle, a rectangle, a square, an oval, or the like. The dimension of the wire 4, referring to the largest dimension of a cross-section of the wire 4, may be less than 2 millimeters, 1 millimeter, or less than 0.8 millimeters, or less than 0.6 millimeters, or less than 0.5 millimeters, or less than 0.4 millimeters. In some embodiments, the inner diameter of a tube may be approximately 1 millimeter, or approximately 0.8 millimeters, or approximately 0.6 millimeters, or approximately 0.5 millimeters, or approximately 0.4 millimeters, or approximately 0.3 millimeters, or approximately 0.2 millimeters. The wire 4 may be commercially available. The wire 4 may be customarily made for a patient.

Figure 5:
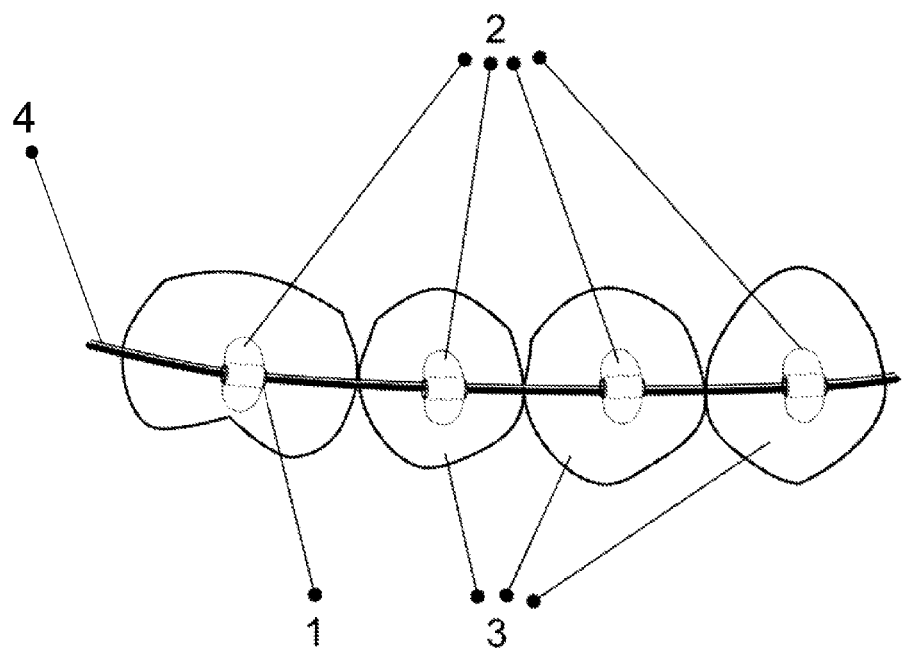
FIG. 5 illustrates a perspective view of some maxillary teeth that are treated with an orthodontic system according to some embodiments of the present disclosure.
Figure 6A:
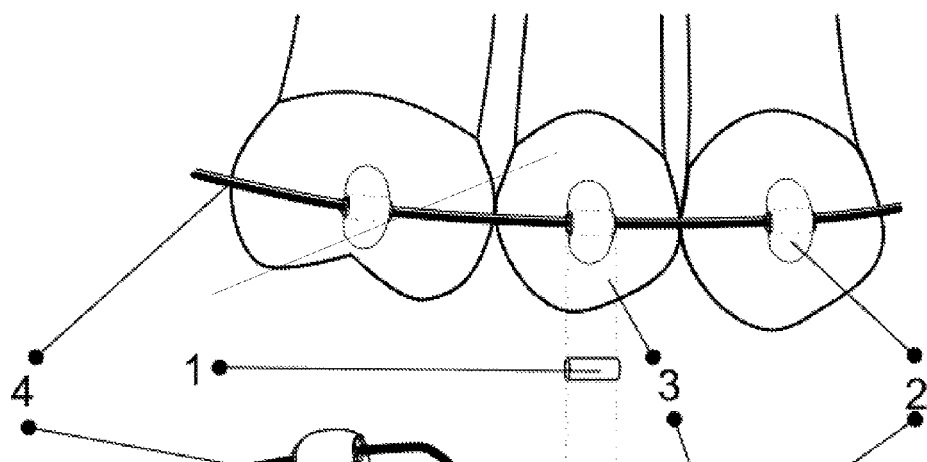
FIG. 6A illustrates a frontal view of some teeth that are treated with an orthodontic system according to some embodiments of the present disclosure.
Figure 6B:
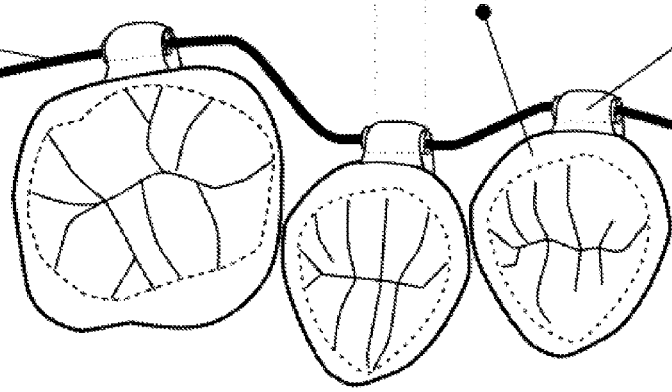
FIG. 6B illustrates a superior view of some teeth that are treated with an orthodontic system according to some embodiments of the present disclosure.

As illustrated in FIGS. 5-6B, an orthodontic system disclosed herein may include a plurality of tubes. FIG. 5 illustrates a perspective view of some maxillary teeth that are treated with an orthodontic system according to some embodiments of the present disclosure. The exemplary orthodontic system illustrated in FIG. 5 may include tubes 1, luting agents 2, and a wire 4. A tube 1 may be directly attached or adhered to a surface of a tooth 3 by the luting agent 2. The tube 1 may be substantially surrounded by or embedded in the luting surround agent 2 disposed on at least a portion of one or more of the at least one sidewall of the tube 1. The luting agent 2 may also be disposed on a portion of the surface of the tooth to which the tube 1 is directly attached or adhered. The two opening ends of the tube 1 may remain substantially open so that a wire 4 may go through and/or move along the tube 1. At least two of the tubes 1 included in the orthodontic system may be different in terms of size (e.g., length, diameter), orientation, or the like, or a combination thereof. These differences of the tubes 1 may be due to considerations including, e.g., the size of the teeth to which the tubes 1 are directly attached or adhere, the grade of misalignment of the teeth, the desired corrections, or the like, or a combination thereof. As the correction of the misalignment of one or more teeth progresses, the orthodontic system may be adjusted by, e.g., adjusting the orientation or the position of one or more tubes 1, adjusting the length of the wire 4, changing an old wire 4 to a new wire 4 which may include a different material, or have a different mechanical property (e.g., elasticity), a different cross-section (from a wire having a circular cross-section to a wire having a rectangular cross-section), or the like, or a combination thereof. One or more of these adjustments may provide an adjustment in the forces imparted to one or more teeth where the orthodontic system is applied.

FIG. 6A illustrates a frontal view of teeth that are treated with an orthodontic system according to some embodiments of the present disclosure. FIG. 6B illustrates a superior view of teeth that are treated with an orthodontic system according to some embodiments of the present disclosure. The exemplary orthodontic system illustrated in FIGS. 6A and 6B may include tubes 1, luting agents 2, and a wire 4. A tube 1 may be directly attached to a surface of a tooth 3 by the luting agent 2. The tube 1 may be substantially surrounded by or embedded in the luting agent 2 disposed on at least a portion of one or more of the at least one sidewall of the tube 1. The luting agent 2 may also be disposed on a portion of the surface of the tooth 3 to which the tube 1 is directly attached or adhered. The two opening ends of the tube 1 may remain substantially open so that a wire 4 may go through and/or move along the tube 1.

Figure 7A:
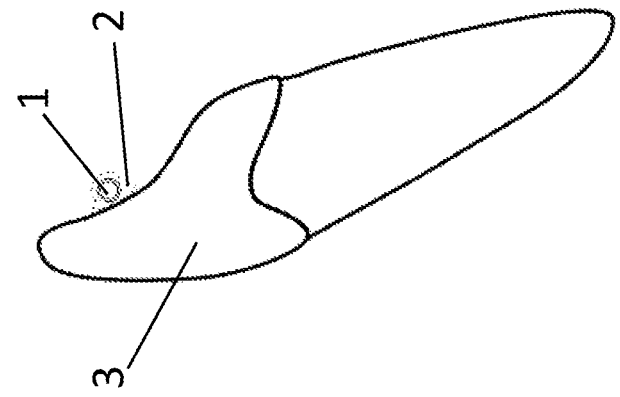
FIG. 7A illustrates an exemplary orthodontic system attached to the labial surface of an incisive tooth.

FIG. 7A illustrates an exemplary orthodontic system attached to the labial surface of an incisive tooth 3. As illustrated, the exemplary orthodontic system may include a tube 1 directly attached to the labial surface of the incisive tooth 3 using a luting agent 2.

Figure 7B:
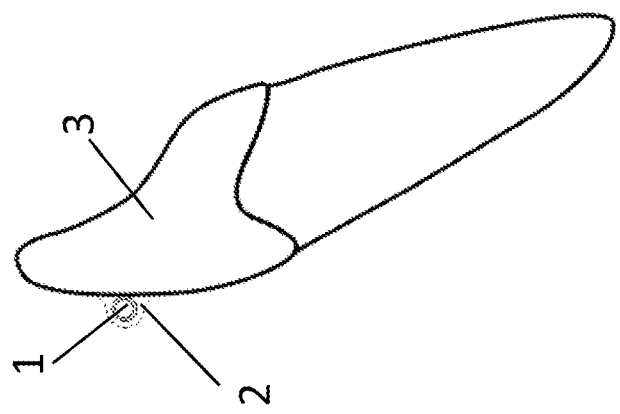
FIG. 7B illustrates an exemplary orthodontic system attached to the lingual surface of an incisive tooth.

FIG. 7B illustrates an exemplary orthodontic system attached to the lingual surface of an incisive tooth 3. As illustrated, the orthodontic system may include a tube 1 directly attached to the lingual surface of the incisive tooth 3 using a luting agent 2.

FIG. 8A illustrates a lateral view of a tooth 3 that is treated with an orthodontic system including a bracket 10. The bracket 10 may include a base 12, and a slot 15. The bracket 10 may be attached to a surface of a tooth 3 at the base 12. The slot 15 may accommodate a wire (not shown in FIG. 8A).

FIG. 8B illustrates a lateral view of a tooth 3 that is treated with an orthodontic system according to some embodiments of the present disclosure. A tube 1 may be directly attached to a surface of a tooth 3 by the luting agent 2.

FIG. 8C illustrates a lateral view of a tooth 3 that is treated with an orthodontic system including a bracket 10. The bracket 10 may include a base 12, and a slot 15. As illustrated, the size of the slot 15 of the bracket 10 may be comparable to the size of a tube 1 according to some embodiments of the present disclosure.

FIGS. 9A-9E illustrate a method of installing the system to perform orthodontics according to some embodiments of the present disclosure. Briefly, the method may include providing a plurality of tubes each of which has at least one sidewall and two opening ends; for each of the plurality of tubes, depositing a luting agent on at least a portion of one or more of the at least one sidewall of the tube and a portion of a surface of a tooth onto which the tube is directly attached or adhered, and curing the luting agent. The two opening ends of a tube may remain substantially open so that a wire may go through and/or move along the tube. The method may also include, e.g., inserting a wire into one or more of the plurality of the tubes, cleaning or etching a surface of a tooth, or the like, or a combination thereof, before applying the luting agent. At least some of the plurality of the tubes 1 may be the same as or similar to those shown in FIGS. 2A-4D. At least some of the plurality of the tubes 1 may include one or more flared end sections as shown in FIGS. 2C, 2D, 3C, and 4A-4D.

FIG. 9A shows cleaning, e.g. by way of etching, a portion 25 of a surface (e.g., a labial surface or a lingual surface) of a tooth 3 using, e.g., an acid conditioner. The portion of the surface to be cleaned or etched may be similar to or slighter larger than the area on the surface of the tooth where the luting agent may cover, which in turn may depend on the size and location of the tubes used in the method. The acid conditioner may include, e.g., 37% phosphoric acid, and may be applied using a brush or tool 20. The etching may take, e.g., 5 to 10 seconds. FIG. 9B shows rinsing the etched portion of the surface of the tooth 3 using, e.g., water 35, via a water spray gun 30. The rinsing may take, e.g., 30 to 40 seconds. The etching using an acid conditioner may create a (partially) demineralized surface including micropores that may be impregnated by a luting agent, e.g., a liquid or flowable resin with low viscosity. When the luting agent hardens or cures inside the micropores produced by the etching, micrometric mechanical lock may be created, thereby inducing adhesion.

FIG. 9C shows positioning a tube 1 on or close to the etched portion of the surface of the tooth 3. The positioning the tube 1 may include, e.g., choosing a desired location, a desired orientation, or the like, for the tube 1, in order to achieve the desired correction of misalignment of the tooth 3 according to the information given by a treatment plan. A wire 4 may be inserted into the tube 1 before the tube 1 is located and adhered to the surface of the tooth 3 using a luting agent 2, as illustrated in FIGS. 9C and 9D. Alternatively, the wire 4 may be inserted into the tube 1 after the tube 1 is located and adhered to the surface of the tooth 3 using the luting agent 2.

FIG. 9D shows depositing a luting agent 2, e.g., a flowable resin, using a charged syringe of resin or a tool 40, on at least a portion of one or more of the at least one sidewall of the tube 1 and the cleaned or etched portion of the surface of the tooth 3 onto which the tube is to be directly attached or adhered. The luting agent 2 may be trickles downwards or upwards, relative to the position of the tube 1, to substantially cover the tube 1. The shape of the luting agent drop (of proper viscosity), may be maintained so as to avoid, e.g., the luting agent 2 from seeping and blocking (partially or completely) either one of the two opening ends of the tube 1, or blocking (partially or completely) the tubular passage of the tube 1. The luting agent 2 may cover a substantial portion of the at least one sidewall of the tube 1 along the length of the tube 1. Merely by way of example, the luting agent 2 may cover at least 30%, 40%, 50%, 60%, 70%, 80%, 90% or more of the surface area (defined by the outer wall(s)) of the at least one sidewall of the tube 1. The tube 1 may be substantially surrounded by or embedded in the luting agent 2. The two opening ends of the tube 1, as well as the tubular passage of the tube 1, may remain substantially open such that the wire 4 may go through and/or move along the tube 1.

FIG. 9E shows curing the luting agent 2 so that the tube 1 may be directly attached or adhere to the surface of the tooth 3. As illustrate, the luting agent 2 may be light curable by photo-polymerization. The curing may be achieved by directing light beams 55 from, e.g., a halogen lamp 50, at the luting agent 2. If the luting agent 2 is, e.g., self-cure or dual-cure, an appropriate curing method may be applied.

The procedure illustrated in FIGS. 9A-9E may be repeated for each tooth where the orthodontics is to be performed.

Some embodiments of the present disclosure relate to a method for performing orthodontics. The method may include providing a plurality of tubes each of which has at least one sidewall and two opening ends, one or more of the at least one sidewall having a pre-applied luting agent; for each of the plurality of tubes, pressing one of the one or more of the at least one sidewall against a surface of a tooth so that the pre-applied luting agent attaches the tube directly onto the surface, and curing the pre-applied luting agent. The two opening ends of a tube may remain substantially open so that a wire may move along the tube. The method may also include, e.g., inserting a wire into one or more of the plurality of the tubes, cleaning or etching a surface of a tooth, or the like, or a combination thereof before applying the luting agent. The wire may be inserted into one or more of the plurality of tubes, before that the tube or the plurality of the tubes are positioned and attached to the surface of the tooth using the luting agent. Alternatively, the wire may be inserted into the tube after the tube is positioned and attached to the surface of the tooth using the luting agent. At least some of the plurality of the tubes 1 may be the same as or similar to those shown in FIGS. 2A-4D. At least some of the plurality of the tubes 1 may include one or more flared end sections as shown in FIGS. 2C, 2D, 3C, and 4A-4D.

In some embodiments, the method for performing orthodontics may further include placing, to a side of the dental arch, a tube to a tooth (or a part of the dental arch) distal to the most posterior teeth involved in a treatment (molar or premolar). In an initial stage, such a tube may provide a posterior guidance to the tubes inserted in the arch wire, to be subsequently attached to the teeth involved in the treatment.

A wire may be inserted into one or more tubes after several or all of the plurality of tubes are positioned and attached to the teeth using a luting agent and the luting agent is cured. A wire may be inserted into one or more tubes before several or all of the plurality of tubes are positioned for attachment by, e.g., depositing and curing the luting agent.

As the correction of the misalignment of one or more teeth progresses, the orthodontic system may be adjusted by, e.g., adjusting the orientation of one or more tubes (by way of, e.g., detaching an old tube, and repositioning the old tube without removing it out of the arch or replacing it with a new tube, and attaching the repositioned or new tube to a surface of the tooth according to a method disclosed herein), adjusting the length of the wire, changing an old wire to a new wire which may comprise a different material, or have a different mechanical property (e.g., elasticity), a cross section of a different caliber, or a different cross-section (from a wire having a circular cross-section to a wire having a rectangular cross-section), or the like, or a combination thereof. Adjusting the length of the wire, or replacing the old wire with a new wire, may be achieved without removing or detaching the tubes. Merely by way of example, the length of the wire may be adjusted by removing a portion of the wire at one end of the wire. As another example, replacing the old wire with a new wire may be achieved by, e.g., removing the old wire, and inserting a new wire into the tubes already in place. One or more of these adjustments may provide an adjustment in the forces imparted to one or more teeth where the orthodontic system is applied.

A conventional system of brackets may be directly installed in the whole dental arch, in only one step and clinical appointment, or it may be indirectly installed in dental models made from impressions taken previously. In the indirect method, brackets are placed in the desired positions on a dental model of teeth of a patient. This may be done while the patient is not present. Afterwards the impression of the dental model with brackets may be taken, using a transfer tray and a proper impression material, and the brackets may be placed, attached or adherer onto the teeth of the patient. Both direct and indirect methods are applicable with the orthodontic system disclosed herein.

Merely by way of example, an exemplary assembly method includes the following steps:
1. preparing the simplified orthodontic system and inserting a wire-arch (e.g., a wire) into the tubes;
2. preparing and etching the tube surface and the surfaces of the teeth;
3. placing the tubes and the arch-wire in the desired places on the surfaces of the teeth; and
4. applying the luting resin on the tubes and the surfaces of the teeth previously prepared and then letting the resin photo polymerize.

Some embodiments of the present disclosure relates to a method for providing a tube to be used in an orthodontic treatment on one or more teeth of a patient. The method may comprise receiving information related to the orthodontic treatment; and providing, based on the information, the tube. The information may include, e.g., the sizes, the colors, the positions (e.g., current and/or desired positions) of some or all the teeth of the patient, an orthodontic treatment plan prepared for the patient, allergy conditions of the patient, preference of the patient regarding, e.g., material or color of the tube to be provided, or the like, or a combination thereof. A tube may have at least one sidewall and two opening ends. A tube may be configured to be directly attached to a surface of a tooth using a luting agent. The two opening ends of the tube may remain substantially open so that a wire can move along the tube, after the tube is attached to a tooth using the luting agent. The tube may comprise one or more flared end sections. The method may further comprise providing the luting agent. In some embodiments, the method may further comprise applying the luting agent to at least a portion of one or more of the at least one sidewall of the tube. In some embodiments, the luting agent may be deposited onto at least a portion of one or more of the at least one sidewall of the tube when the orthodontic treatment is performed. The method may comprise providing, based on the information, a plurality of tubes to be used in an orthodontic treatment on one or more teeth of a patient. The method may further comprise providing a wire.

The foregoing detailed description has set forth various embodiments of the devices and/or processes by the use of diagrams, flowcharts, and/or examples. Insofar as such diagrams, flowcharts, and/or examples contain one or more functions and/or operations, it will be understood by those within the art that each function and/or operation within such diagrams, flowcharts, or examples may be implemented, individually and/or collectively, by a wide range of hardware, software, firmware, or virtually any combination thereof.

Those skilled in the art will recognize that it is common within the art to describe devices and/or processes in the fashion set forth herein, and thereafter use engineering practices to integrate such described devices and/or processes into other orthodontic systems. That is, at least a part of the devices and/or processes described herein may be integrated into an orthodontic system via a reasonable amount of experimentation.

The subject matter described herein sometimes illustrates different components contained within, or connected with, other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

All references, including but not limited to patents, patent applications, and non-patent literature are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following Claims.

What is claimed is:
1. A method for performing orthodontics, comprising:
adhering a first tube to a first tooth situated on a labial side or a lingual side of a dental arch of a patient distal to a most posterior section of teeth involved in a treatment;
adhering a second tube to a second tooth situated on an opposite labial side or an opposite lingual side of the dental arch of the patient, respectively;
providing an arch wire that is inserted through a plurality of tubes, wherein the plurality of tubes are distinct from the adhered first tube and the adhered second tube, each of which comprises at least one sidewall and two opening ends that form a tubular passage adapted to allow the arch wire to move along a length of the tubular passage;
inserting, through the adhered first tube and the adhered second tube, the arch wire including the plurality of tubes; and
subsequent to inserting the arch wire including the plurality of tubes through the adhered first tube and the adhered second tube, adhering each of the plurality of tubes by:
depositing a luting agent on at least a portion of one or more of the at least one sidewall of a tube and a portion of a surface of a tooth onto which the tube is directly attached or adhered, and
curing the luting agent.
2. The method of claim 1, wherein the luting agent comprises flowable resin.

3. The method of claim 1, wherein the luting agent comprise at least one material selected from the group consisting of a light-cure material, a self-cure material, and a dual-cure material.

4. The method of claim 1, wherein the cured luting agent covers more than 50% of the surface area of the at least one sidewall of the tube.

5. The method of claim 1, wherein a sidewall of the tube is in contact and attached to the surface of the tooth using the luting agent or separated from the surface of the tooth by the same luting agent.

6. The method of claim 1, wherein depositing the luting agent comprises depositing the luting agent on either a portion of the labial side of the tooth or a portion of the lingual side of the tooth.

7. The method of claim 1, wherein the tube further comprises one or more flared end sections.

8. The method of claim 1, further comprising etching the portion of the surface of the tooth.

9. The method of claim 1, further comprising adjusting an orientation of one or more tubes during the treatment.

10. A method for performing orthodontics, comprising:
providing a plurality of tubes each of which has at least one sidewall and two opening ends, one or more of the at least one sidewall having a pre-applied luting agent;
inserting a wire through the plurality of tubes; and
for each of the plurality of tubes,
subsequent to inserting the wire through the plurality of tubes, pressing one of the one or more of the at least one sidewall against a surface of a tooth so that the pre-applied luting agent attaches the tube directly onto the surface, and
curing the pre-applied luting agent, wherein the two opening ends remain substantially open so that the wire can move along the tube.

11. The method of claim 10, wherein the luting agent comprises flowable resin.

12. The method of claim 10, wherein the luting agent comprises at least one material selected from the group consisting of a light-cure material, a self-cure material, and a dual-cure material.

13. The method of claim 10, wherein the cured luting agent covers more than 50% of the surface area of the at least one sidewall of the tube.

14. The method of claim 10, wherein a sidewall of the tube is in contact and attached to the surface of the tooth using the luting agent or separated from the surface of the tooth by the same luting agent.

15. The method of claim 10, wherein the pressing comprises pressing against either the labial side of the tooth or the lingual side of the tooth.

16. The method of claim 10, wherein the tube comprises one or more flared end sections.

17. The method of claim 10 further comprising etching a portion of the surface of the tooth.

18. The method of claim 10 further comprising:
prior to inserting the wire through the plurality of tubes,
adhering a first tube distinct from the plurality of tubes to a first tooth situated on a dental arch of a patient distal to a most posterior section of teeth involved in a treatment, wherein the first tube adhered to the first tooth provides a posterior guidance to the plurality of tubes.

19. The method of claim 10, further comprising adjusting an orientation of one or more tubes during treatment.

20. A method for performing orthodontics, comprising:
providing an arch wire that is inserted through a plurality of tubes, each of the plurality of tubes excluding a base, a notch, a wing, or a combination thereof; and
adhering each of the plurality of tubes inserted through the wire to a dental arch of a patient, wherein adhering each of the plurality of tubes includes:
positioning an outer wall of a tube directly over a surface of a tooth of the patient;
substantially surrounding the outer wall of the tube with a resin;
pressing the tube and the resin against the surface of the tooth; and
curing the resin.

21. The method of claim 20, further comprising:
prior to providing the arch wire that is inserted through the plurality of tubes,
adhering a first tube to a first tooth situated on a first side of a dental arch of the patient distal to the most posterior teeth involved in a treatment; and
inserting the arch wire through the first tube, wherein the first tube adhered to the first tooth provides a posterior guidance to the plurality of tubes.

22. The method of claim 21, wherein the first tube is situated on a distal end of the arch wire.

23. The method of claim 21, further comprising adjusting an orientation of one or more of the plurality of tubes during the treatment.

* * * * *